United States Patent [19]

Ciarlei et al.

[11] Patent Number: 4,851,866
[45] Date of Patent: Jul. 25, 1989

[54] AIR VENT FOR CAMERA ADAPTOR

[75] Inventors: Joseph A. Ciarlei, Marcellus; Michael J. Pileski, Warners, both of N.Y.

[73] Assignee: Welch Allyn, Inc., Skaneateles Falls, N.Y.

[21] Appl. No.: 214,312

[22] Filed: Jul. 1, 1988

[51] Int. Cl.$^4$ .......................... G03B 29/00; A61B 1/04
[52] U.S. Cl. .......................................... 354/62; 128/4; 358/98
[58] Field of Search .................. 354/62; 128/4, 5, 6, 128/7, 8; 358/98; 350/588

[56] References Cited

U.S. PATENT DOCUMENTS

| | | | |
|---|---|---|---|
| 832,219 | 10/1906 | Spear | 350/588 |
| 2,465,764 | 3/1949 | Underhill, Jr. | 350/588 |
| 3,900,021 | 8/1975 | Makepeace et al. | 128/4 |
| 4,264,167 | 4/1981 | Plummer | 354/62 |
| 4,305,386 | 12/1981 | Tawara | 354/62 |
| 4,318,395 | 3/1982 | Tawara | 354/62 |
| 4,478,212 | 10/1984 | Asano | 354/62 |
| 4,539,586 | 9/1985 | Danna et al. | 128/6 |
| 4,590,923 | 5/1986 | Watanabe | 358/98 |
| 4,655,569 | 4/1987 | Sims | 354/62 |
| 4,722,000 | 1/1988 | Chatenever | 358/98 |
| 4,794,913 | 1/1989 | Shimonaka et al. | 128/4 |

*Primary Examiner*—A. A. Mathews
*Attorney, Agent, or Firm*—Wall and Roehrig

[57] ABSTRACT

An adaptor for coupling an endoscopic probe to a video processor for displaying a picture of a target upon a viewing screen. The probe contains an optical element at its proximal end for providing an image of the target. A camming mechanism is used to secure the proximal end of the probe in one end of the adaptor housing. A small camera having a solid state in an insertion barrel is attached to the adaptor housing by sliding the lens barrel into a receiving opening formed in the opposite end of the housing. A chamber separates the distal end of the lens barrel and the proximal end of the probe. The targeted image presented by the optical element of the probe is recorded upon an imager mounted in the camera lens barrel and transmitted to the processor for viewing on the screen. The lens barrel is held within the adaptor housing by a detent mechanism having a ball that engages a groove formed in the lens barrel. A hollow stud having an axial bore is threaded into the adaptor housing so that the stud passes into the ball seat. A spring is contained within the bore which urges the ball into engagement with the lens barrel. An air passage connects the bore of the stud with the chamber separating the camera lens barrel and the probe whereby any moisture accumulating within the chamber is drawn out of the adaptor housing by applying suction to the stud.

6 Claims, 2 Drawing Sheets

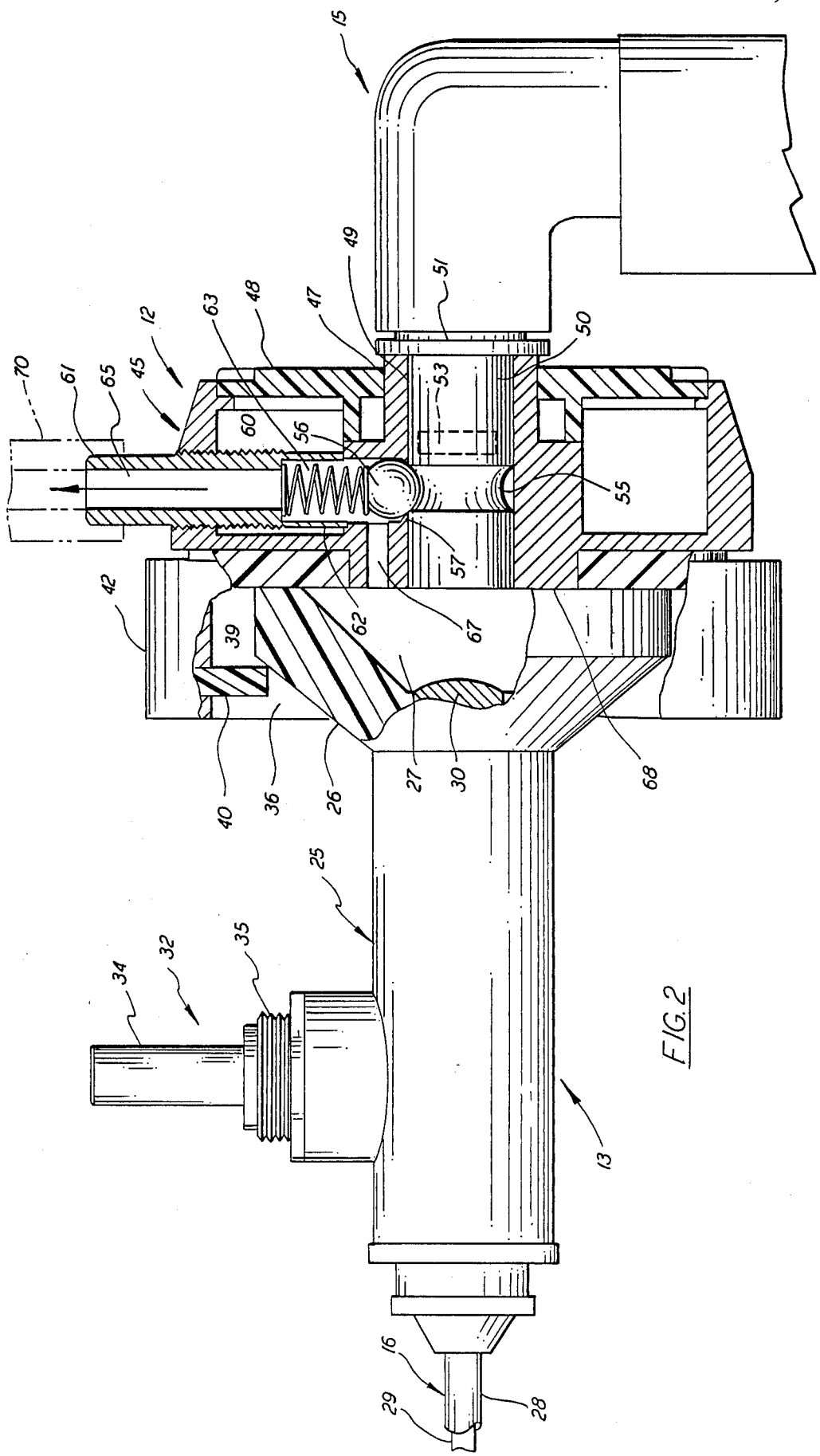

AIR VENT FOR CAMERA ADAPTOR

BACKGROUND OF THE INVENTION

This invention relates to apparatus for coupling a small video camera to an optical endoscopic probe to enable the optical image produced by the probe to be converted to a video picture.

Sims in U.S. Pat. No. 4,655,569 discloses an eyepiece adaptor for coupling an optical endoscope to the lens barrel of a self-contained camera. The adaptor is threaded into the lens barrel of the camera and the proximal end of the endoscope is inserted into the front of the adaptor. A split-collar is passed over the probe and threaded into the front of the adaptor to lock the probe in alignment with the camera lens. Once the probe is locked in place, moisture can be trapped in the region separating the endoscope and the camera lens barrel. Any moisture in this area will coat the exposed optical elements and thus seriously degrade the target image. When this occurs, the adaptor must be dismantled and the optical element cleaned.

Makepeace et al, in U.S. Pat. No. 3,900,021 also describes a similar adaptor for coupling an endoscope to a self-contained camera. The adaptor has a magnetic coupling that permits the endoscope to be rotated about the camera lens axis. Here again, no provision is made for removing moisture that might have developed inside the adaptor housing and the exposed optical elements will become contaminated as moisture builds up in this region.

Underhill Jr., in an earlier U.S. Pat. No. 2,465,764 describes a cylindrical lens barrel for use in a motion picture camera. The lens barrel is arranged to conduct light from a high intensity lamp to a film strip so as to project an image of the data recorded on the film strip to a viewing screen. As noted by Underhill Jr., oil used in this type of motion picture camera oftentimes finds its way into the lens system and coats the optical elements. Underhill Jr. passes a small relief tube into his lens barrel which allows air to pass into and out of the barrel. When the optical elements within the barrel are heated by the lamp, ambient air is drawn into the barrel through the tube. The air is later expelled when the lamp is turned off and the barrel cools. This constant exchange of air permits the barrel to "breathe" and thus expel unwanted oil collected in the lens barrel. The tube is packed with absorbent material which collects the expelled oil. Most modern-day cameras, and in particular, solid state cameras, are not subjected to oil contamination nor are they subjected to extreme changes in temperatures. The breathing technique described by Underhill Jr. therefore is of little or no use in these types of cameras.

Camera adaptors have been developed for use in endoscopes which are capable of coupling an optical probe to a video system so that an enlarged picture of the target can be presented upon a television screen. The proximal end of the probe is generally relatively small and, as a consequence, the adaptors are correspondingly small. Little room is thus afforded within the adaptor for mounting apparatus for preventing or removing moisture. Attempts directed toward locating this type of equipment within this limited space, have proven to be generally unsatisfactory.

SUMMARY OF THE INVENTION

It is therefore an object of the present invention to improve camera adaptors used in endoscopic systems.

It is a further object of the present invention to more efficiently remove moisture from a camera adaptor that is used to couple an endoscopic probe to the lens barrel of a video camera.

A still further object of the present invention is to provide a camera adaptor for use in an optical endoscope that has a mechanism for securing the video camera within the adaptor and through which moisture can be removed from the adaptor without disconnecting the adaptor.

These and other objects of the present invention are attained by means of an adaptor for coupling an optical endoscopic probe to a video camera so that a picture of the target can be presented on a television screen. The endoscopic probe has an imaging lens mounted in the proximal end thereof that is surrounded by a radially disposed flange. The adaptor includes a camming mechanism for engaging the flange of the probe and locking the end face of the flange against the housing. The video camera has a lens barrel that is inserted into an opening formed within the adaptor. In assembly, a chamber separates the imaging lens of the probe and the distal end of the camera lens barrel. The lens barrel is held in the adaptor by a detent mechanism that includes a ball for engaging the barrel that is contained in a ball seat. A hollow venting stud is passed inwardly through the adaptor into the detent ball seat. The stud contains an axial bore that houses a biasing spring for urging the ball into engagement with the camera lens barrel. An air passage is formed in the adaptor that connects the bore of the venting stud and the chamber separating the imaging lens of the probe and the camera lens barrel so that any moisture collected within the chamber region can be drawn out the adaptor through the hollow stud by applying suction to the stud.

BRIEF DESCRIPTION OF THE DRAWINGS

For a better understanding of these and other objects of the present invention reference will be made to the following detailed description of the invention that is to be read in association with the accompanying drawings, wherein FIG. 2 is an enlarged side elevation in partial section showing the camera adaptor connected to an arthroscopic probe of a video system.

DESCRIPTION OF THE INVENTION

Figure 1:
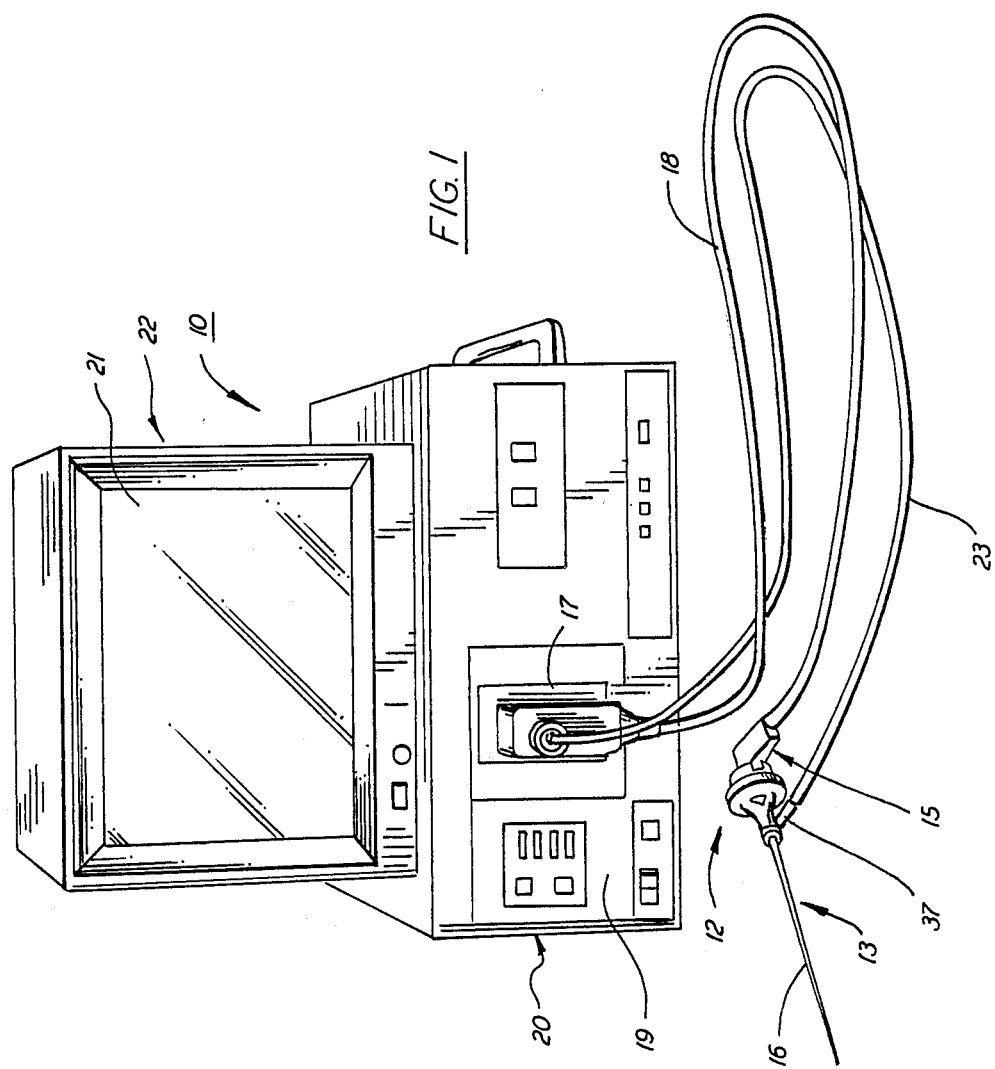
FIG. 1 is a perspective view of a video equipped endoscope having a camera adaptor embodying the teachings of the present invention.

Turning initially to FIG. 1, there is shown a video equipped endoscope generally referenced 10 that includes a camera adaptor 12 embodying the teachings of the present invention. An arthroscopic probe 13 is mounted in the front of the adaptor while a small video camera 15 is passed into the adaptor housing through the rear wall thereof. As will be explained in greater detail below, the arthroscopic probe contains a small diameter insertion tube 16 having a fiber bundle enclosed therein which brings light to a target region situated in front of the probe and returns a light image of the target to an imaging lens located at its proximal end. The camera houses a solid state imager that is adapted to record the target presented at the imaging lens of the probe and converts the recorded image data to an electrical output signal that is capable of being accepted by the video processor.

The video camera 15 is coupled to a connector module 17 by means of an umbilical cord 18. The connector module is plugged into the front face 19 of a video processor 20 wherein the electrical signals fed from the imager are placed in a format for presentation upon the viewing screen 21 of a television monitor 22. Light for illuminating the target region is transmitted from a high intensity lamp (not shown) located in the processor through the connector module to the endoscopic probe by means of a flexible light pipe 23. As can be seen, the camera adaptor is relatively small and provides little room for accommodating equipment for either controlling or removing moisture that might collect inside the adaptor.

With further reference to FIG. 2, the proximal end of the arthroscopic probe contains a cylindrical rear section 25 that terminates with a radially disposed circular flange 26 defining a recessed lens chamber 27. The insertion tube 16 of the probe includes a metal outer sheath 28 that surrounds a fiber bundle 29. As noted, the fiber bundle functions to bring light into the target region of the probe and an image of the target back to an imaging lens 30 centrally mounted at the proximal end of the probe within the lens chamber. A coupling 32 is mounted on the rear section 25 of the probe that includes a light input tube 34 and a threaded connector 35. In assembly, the light exit end 37 of light pipe 23 (FIG. 1) is passed over the input tube 34 and is threaded onto the connector 35 to provide a light tight connection. Light from the processor is passed through the coupling into the probe where it is projected by the fiber bundle through the distal end of the probe to illuminate the target region.

The front face of the adaptor has a receiving opening 36 formed therein into which the circular flange of the probe is inserted. In assembly, the rear wall of the flange is seated securely against the back wall 39 of the receiving opening. A series of circumferentially spaced locking tabs 40 protrude downwardly into the receiving opening from a circular camming mechanism 42 that is mounted for rotation about the axis of the adaptor. The camming mechanism is spring biased into a home position wherein the locking tabs are normally extended into the flange engaging position shown in FIG. 2. When the tabs are extended in contact with the probe flange, the probe is securely centered against the back wall 39 of the receiving opening. By turning the camming mechanism against the biasing action of the spring, the locking tabs are retracted to a release position whereby the probe can be removed from the adaptor. The adaptor further contains a cylindrical metal support frame 45 that includes a centrally located hollow tube 47 that opens through the rear wall 48 of the adaptor and is mounted flush with the back wall 39 of the probe receiving opening 36. The tube contains a circular opening 49 for receiving lens barrel 50 of the video camera 15 therein. A radially disposed stop-ring 51 is secured to the barrel which, in assembly, contacts the rear wall of the adaptor and thus controls the depth to which the camera can penetrate into the opening 49. A small solid state imager 53 is mounted inside the lens barrel and is arranged to record the image presented at the imaging lens 30 of the probe. The recorded image information is converted into electrical signals which are transmitted back to the video processor 20 where the data is placed in a format for presentation upon the monitor screen 21.

The lens barrel 50 of the camera is furnished with a circular grove 55 that is adapted to mate with a detent ball 56 (FIG. 2) when the lens barrel is fully inserted into the adaptor. The ball is mounted within a circular seat 57 formed in the wall of tube 47. The ball is biased against the seat by means of a compression spring 60 so that a portion of the ball protrudes into the opening 49 to engage the barrel grove 55 and thus hold the camera securely within the adaptor.

A hollow stud 61 is threaded radially into the metal frame 45 of the adaptor so that the lower end 62 of the stud passes into a complimentary opening formed in the top of the ball seat. The stud, in assembly is lightly pressfitted into the ball seat to provide a relatively fluid tight joint therewith. The stud has an axially aligned bore 65 passing therethrough which terminates in an expanded opening 63 that is positioned immediately over the ball 56. The compression spring 60 is mounted within the expanded opening in a loaded condition to continually urge the ball into the ball seat. An axially disposed air passage 67 is formed in the frame 45 of the adaptor that passes from the, front end face 68 of the frame into the ball seat. The air passage serves to place stud bore 65 in direct communication with the lens chamber 27. Accordingly, air can be freely circulated through the hollow stud into the lens chamber thereby helping to prevent moisture from building up in this critical region. As noted, any moisture found in this region will not only coat the imaging lens of the probe but also any exposed optical elements mounted within the camera lens barrel thereby degrading the video picture present upon the monitor screen.

In the event moisture does accumulate within the lens chamber, it can be drawn out of the adaptor by simply applying a suitably-sized suction tube 70 over the extended end of the stud. By applying a slight amount of suction to the stud bore moisture collected in the chamber will be quickly withdrawn from the housing without having to remove the probe or camera from the adaptor.

While this invention has been described with specific reference to the details as set forth in this application, the invention is broad enough to encompass any combination of elements coming within the scope of the claims.

What is claimed is:

1. An adaptor for connecting a probe having an optical read-out element at the proximal end thereof to the cylindrical lens barrel of a video camera, said adaptor including a housing having locking means for engaging the proximal end of the probe and an opening for slidably receiving the lens barrel of the camera so that a chamber separates the optical read-out element of the probe and the distal end of the lens barrel, a detent means that contains a ball mounted in a seat formed in said housing, said ball being arranged to engage the lens barrel, a hollow member mounted in said housing, said member having an axial bore and a distal end that passes into said seat and a proximal end that protrudes outwardly from the housing, spring means mounted in said bore that acts upon said ball to urge said ball into said seat, an air passage formed in the housing for connecting the chamber and the bore formed in said member so that moisture formed in the chamber can be drawn out of the housing through said member.

2. The apparatus of claim 1 wherein said hollow member is a stud that is threadably received within said housing.

3. The apparatus of claim 1 wherein said ball is adapted to ride in a groove formed in the camera lens barrel.

4. The apparatus of claim 1 wherein said air passage passes through the seat formed in the housing.

5. The apparatus of claim 2 wherein said biasing means is a spring which is mounted within an expanded chamber formed in said stud.

6. The apparatus of claim 1 wherein said locking means includes cam-actuated tabs for releasably engaging the proximal end of a probe.

* * * * *